United States Patent [19]

Bentley

[11] Patent Number: 4,661,984

[45] Date of Patent: Apr. 28, 1987

[54] LINE INSPECTION SYSTEM

[76] Inventor: William A. Bentley, 170 The Masters Cir., Costa Mesa, Calif. 92627

[21] Appl. No.: 70,899

[22] Filed: Aug. 29, 1979

Related U.S. Application Data

[63] Continuation-in-part of Ser. No. 803,360, Jun. 3, 1977, abandoned.

[51] Int. Cl.$^4$ .............................................. G06K 9/00
[52] U.S. Cl. ..................................... 382/8; 356/237; 382/65
[58] Field of Search ................... 340/146.3 E, 146.3 H, 340/146.3 AE, 146.3 AC, 146.3 F, 146.3 R; 364/515; 250/560, 562, 563, 572; 356/372, 376, 381–387, 394, 237; 235/92 PC; 358/106; 382/65, 8

[56] References Cited

U.S. PATENT DOCUMENTS

| | | | |
|---|---|---|---|
| 2,958,464 | 11/1960 | Nassenstein | 235/92 PC |
| 3,541,510 | 11/1970 | Nishioka | 340/146.3 AE |
| 3,563,666 | 2/1971 | Foster | 250/560 |
| 3,611,290 | 10/1971 | Luisi et al. | 340/146.3 E |
| 3,620,629 | 11/1971 | Whittington | 250/560 |
| 3,647,961 | 3/1972 | Blitchington et al. | 358/106 |
| 3,671,941 | 6/1972 | Takahashi et al. | 340/146.3 AE |
| 3,873,974 | 3/1975 | Bouton et al. | 340/146.3 AC |
| 4,021,778 | 5/1977 | Ueda et al. | 340/146.3 AC |
| 4,083,035 | 4/1978 | Riganati et al. | 340/146.3 E |
| 4,109,237 | 8/1978 | Hill | 340/146.3 E |
| 4,170,003 | 10/1979 | Danielsson et al. | 340/146.3 H |
| 4,223,387 | 9/1980 | Danielsson et al. | 364/515 |

FOREIGN PATENT DOCUMENTS 1431438  4/1976  United Kingdom ...... 340/146.3 AC Primary Examiner—Leo H. Boudreau
Attorney, Agent, or Firm—Spensley Horn Jubas & Lubitz

[57] ABSTRACT

A line inspection system suitable for inspecting printed circuit boards for defects. In a first embodiment disclosed, a plurality of sensors which detect the presence or absence of conductor material on the board are grouped in a preestablished pattern. The area of the circuit board to be inspected is scanned by the sensing pattern and logical sequences of sensor condition which indicate defects are searched for. In a second embodiment disclosed, the area to be inspected is scanned serially, and the resultant data stored. Logical analysis is then performed on the stored data to determine whether the pattern of data is or is not consistent with an acceptable part.

70 Claims, 9 Drawing Figures

LINE INSPECTION SYSTEM

BACKGROUND OF THE INVENTION

1. Related Applications

This is a continuation in part of application Ser. No. 803,360 filed June 3, 1977, now abandoned.

2. Field of the Invention

This invention relates generally to pattern recognition devices and more particularly to devices for locating defects in line patterns as, for example, conductor patterns on printed circuit boards.

3. Prior Art

An important step in the production of printed circuit boards as used in modern electronic assemblies is the inspection of the board for defects. These defects may take many forms, such as cracks, pinholes or voids in the conductors, bridges between conductors, tendrils, undersized traces, etc. Traditionally, the inspection task has been done by visual observation, and thousands of such inspectors are currently employed in the printed circuit board industry. It is obviously important to find circuit pattern defects before the electronic components are installed, since the net cost of a defect is much higher later. The inspection step itself, which depends on human labor, forms a substantial part of the cost of the board, and small defects in particular are often missed by the human inspectors. It is therefore an object of the present invention to provide a machine to inspect circuit boards inexpensively, automatically, and thoroughly, so as to reduce the net costs of the boards and to increase their reliability.

SUMMARY OF THE INVENTION

The defects searched for by the present invention are, in general, the smaller defects that may easily escape the attention of human inspection. Such defects include small holes in the conductors, nicks, breaks, narrow conductors, extraneous metal on the board, and conductors too closely spaced. The inspection machine of the present invention does not rely on a knowledge of the required trace pattern, but only a knowledge of the characteristics of acceptable patterns. Thus, the inspection cycle, once set up, can be used to inspect many different boards having a wide variety of circuits thereon, without change in the setup.

In the preferred embodiments of the invention herein disclosed, commonly accepted criteria for acceptance of an electronic printed circuit board are utilized by way of example to illustrate the principles of the invention. It should be understood that other criteria may be applicable in particular applications, in which case sensing patterns other than those disclosed, and other logic sequences for acceptance or rejection may be required to perform the inspection. It should also be understood that while presently preferred sensing patterns and logic sequences are disclosed herein by way of example, various sensing patterns and/or logic sequences could be used in connection with the illustrative criteria or any other particular set of criteria.

The characteristics of an acceptable conductor on a printed circuit board utilized by way of example herein are:

1. The normal conductor has a minimum acceptable width. (The machine of this invention may be set to accomodate any desired value.)

2. The spacing between conductors has a certain minimum value, typically one minimum conductor width.

3. No extraneous conductor material may be closer to any conductor than the minimum conductor spacing.

4. No breaks, nicks or holes in any conductor are allowable.

5. No tendrils on conductors or bridges between conductors are allowable.

6. Each trace must terminate in an enlarged pad at each end.

In accordance with the first scanning method to be disclosed, the area of the board to be inspected is scanned in much the same way as a television image, by a plurality of sensors spaced in a preestablished pattern. The spacings and arrangement of the sensors are such that any deviation from the acceptable characteristics established for the traces on the board being inspected results in certain logical sequences of sensor operation. Conventional logic circuitry is used to analyze the sequences and thus indicate defects. As desired, the logic circuitry can be used to activate alarm circuitry so as to reject defective boards, or to enable the marking of the location of the defect on the board itself, on an inspection report, or on other display devices. Various display, recording, and/or control devices suitable for use with the present invention will occur to those skilled in the art.

In accordance with one presently preferred embodiment of the invention, utilizing the first method of scanning, points within a small circular area having a diameter approximately three times the minimum width of a trace are simultaneously viewed, and the pattern of conductor areas as existing at 36 points within the area are analyzed by the logic circuitry to determine whether the board area as viewed contains such conductor areas as are consistent with a satisfactory printed circuit board. Certain conductor patterns within the viewed area are known to indicate a defective board, and these patterns are detected by the logic circuitry. The entire circuit board area is rapidly scanned so that each point on the board is inspected for conformance to the established criteria in a short period of time.

The scanning function may be accomplished by directing a beam of light, originating at a laser, through appropriate lenses onto a mirrored rotating tetrahedron and thence by reflection onto the board being inspected. The rotating tetrahedron causes the spot of light falling on the board to scan a line across the board repeatedly, and a motor drive moves the board being inspected linearly at right angles to the line scan, thereby creating a scanning raster.

Light reflected off the spot on the board is reflected back up to the tetrahedron and is thence directed through other lenses which focus an image of the board onto a sensor assembly. Zoom lenses are used in the system so that the image size needed to accommodate the detection requirements for the particular trace being inspected can be achieved.

A second embodiment of the scanning function utilizes a line scanner or a "flying spot" scanner to scan all of the points in the area being inspected sequentially. The resulting data is stored in a memory comprised of a group of shift registers. The data in selected stages of the shift registers are outputted in parallel, resulting in a group of signals similar to that provided by the first scanning embodiment. These signals may be logically analyzed in the same manner as used with the first embodiment.

DETAILED DESCRIPTION OF THE INVENTION

The present invention involves the application of logical analysis to patterns of sensed points on a printed circuit board under test to establish whether or not previously established criteria are met by the traces on the board. If the criteria are not met in any region of the board, a defect is indicated. As will be discussed in detail below, every point in the area to be inspected is sensed, and each sensed point is used in combination with other sensed points to form the patterns which indicate whether or not the criteria have been met. In one embodiment of the invention all of the points in the area being inspected are sensed serially in a manner similar to a television scene, and the resulting data stored in a memory. The patterns of points to be analyzed are subsequently created from the stored data. Alternatively, a plurality points having the geometrical relationships from which the patterns can be formed may be sensed simultaneously by a group of sensors, and the circuit board scanned by this group. This latter approach allows the logical analysis to be applied to the data as it is developed without the need for memory means.

For purposes of ease of explanation, the presently preferred patterns of sensed points, and the logical sequences which establish whether or not a defect exists, will be explained assuming that all of the points are sensed simultaneously, and the logic applied to the instantaneous condition of the sensors. It will be understood that the points could also be scanned serially as mentioned above and operated on logically at a later time.

Figures 1, 2:
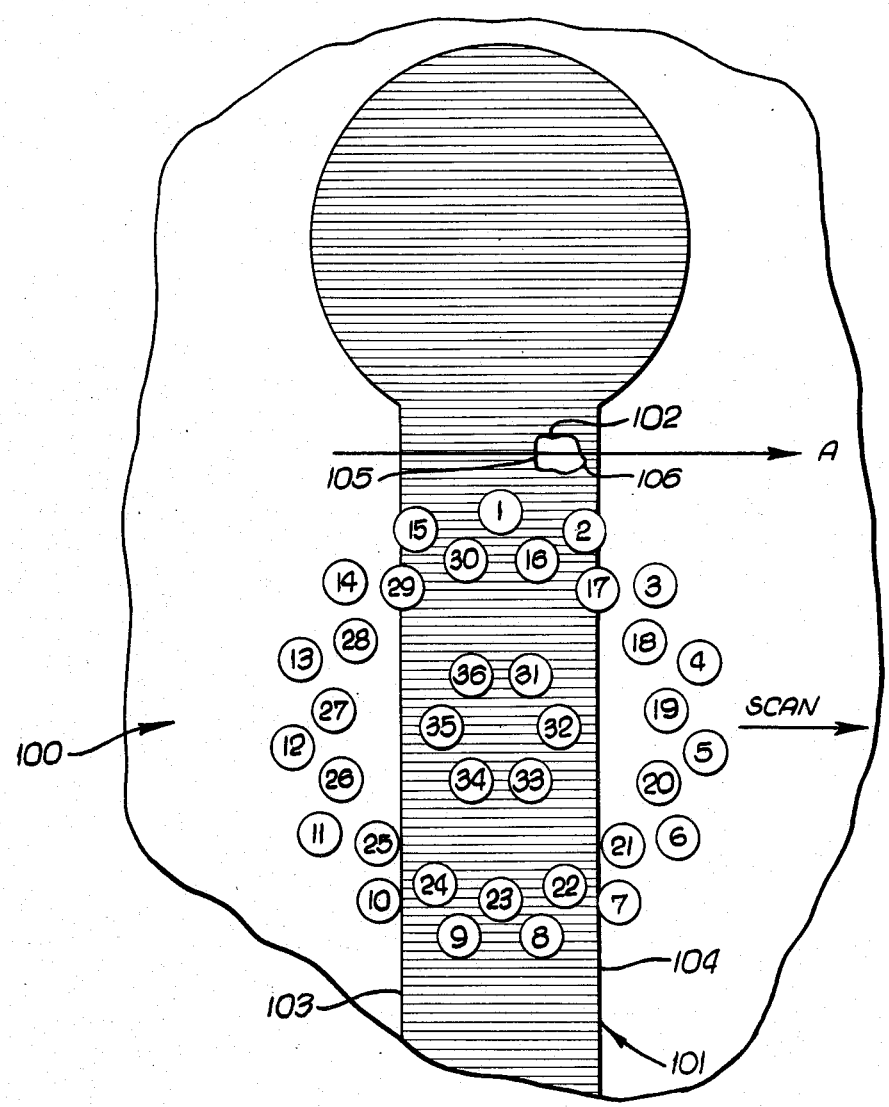
FIG. 1 is a face view of the sensor assembly of a first embodiment of the invention with the image of a portion of a circuit board being inspected superimposed thereon.
FIG. 2 is a face view of the sensor assembly of a first embodiment of the invention with a defective trace superimposed thereon.

Referring now to FIG. 1, which can be visualized as a plan view of a portion of a printed circuit board 100 containing a trace 101 having a width equal to the minimum trace width. The circles 1 through 36 represent sensors, each of which observes the area within the circle to determine whether or not the area observed is occupied by a conductor or substrate. The sensors are either "on" or "off", "on" meaning that one half or more of the observed area is occupied by conductor, and "off" indicating that less than one-half of the area is occupied by conductor.

The actual construction of two embodiments of the scanning portion of an apparatus according to the invention will be described below, but for the purposes of understanding the principles of the invention, the scanning function can be thought of in operational terms as if a group of sensors of appropriate size, as an assembly, is repeatedly passed over the circuit board being inspected (the assembly being displaced slightly at right angles to the direction of scan after each pass) until each sensor of the group has scanned the entire board area. The sensors of the sensor assembly are grouped in a preestablished configuration so as to detect image patterns which are inconsistent with the established criteria. It is convenient to utilize light to oprate the sensors, but it will be clear to those skilled in the art that other types of sensing means such as electrical contacts, pneumatic sensors, etc. could be used in various applications.

The sensing array of sensors 1 through 36 has a particular geometrical configuration determined by the particular defects intended to be detected as will be described below. The number and configuration of sensors in the sensing array which has been chosen as an example for purposes of explanation is comprised of two concentric circles of 15 sensors each, and an inner circle comprised of 6 sensors. The spatial relationships of the various sensors 1 through 36 remains constant throughout the inspection cycle, an inspection cycle consisting of scanning the area to be inspected with the sensing paattern in much the same way as a television picture is scanned. For purposes of explanation, the direction of scan will be taken to be in the direction as shown in the Figures. That is, assuming the board 100 is stationary, the sensing pattern will traverse the board in the direction shown, with the sensors turning on and off as the conductor edges are passed. After each pass of the sensing pattern, the pattern is indexed a small amount downward, for example one circle diameter. A complete inspection cycle consists of as many passes as are necessary to cover the area being inspected. Vertical line A identifies the locus of sensor 1 on particular passes to be described below to explain the operation of the invention. It is not necessary that this particular scanning plan be used, or even that a consistent plan be used. It is only necessary that during the inspection cycle the entire area to be inspected be viewed.

One type of defect which often appears on printed circuit boards is a conductor which has a width narrower than the minimum acceptable. This defect may be detected by the operation of sensors 1, 17 and 29 as shown in FIG. 1. The radius of the circle of sensors 16 through 30 is set such that the spacing of sensors 17 and 29 is equal to the minimum conductor width, that is, the radius equals about 0.85 times the minimum conductor width. Sensor 1, on the outer circle of sensors, is located midway between sensors 17 and 29. It can be seen that the logical combination of sensor 1 on, while both sensors 17 and 29 are off, indicates that the trace width is below the minimum allowable. This is so since if the conductor width is greater than the spacing between sensors 17 and 29, either 17 or 29, or both, will be on whenever 1 is on. On the other hand, if the conductor were narrower than the minimum allowable conductor width, there would be a time while sensor 1 is on that both 17 and 29 are off.

While in the presently preferred embodiment shown herein, sensor 1 is shown equidistant from sensors 17 and 29, it is not necessary that such be the case. It is only necessary that sensor 1 be "between" sensors 17 and 29. By "between" is meant in the region bounded by the perpendiculars to the line joining sensors 17 and 29 through sensors 17 and 29.

It may be noted that it is not necessary to adjust the sensor positions to achieve the desired spacing of the sensors relative to the minimum trace width. In a presently preferred embodiment of the invention described below, the size of an image of the board under test on the assembly of sensors is varied to achieve the desired relative spacing. For purposes of explanation, however, it is convenient to think of the sensor array as being sized to suit the circuit board criteria.

The same logic will detect a void in the conductor such as void 102. As the line of sensors containing sensors 17 and 29 scans line A, for example, sensor 17 will come on at edge 103, go off at edge 105, on again at edge 106, and finally off at edge 104. Depending on the size of void 102, sensor 1 will either follow the same sequence, but later in time, or simply come on at edge 103 and off again at edge 104. Sensor 29 will start the same sequences as sensor 17 slightly before sensor 17 goes off at edge 119, assuming that the conductor width is greater than minimum. If the void 102 is large enough to make the net conductor section less than minimum, there will be a time while sensor 17 is off due to void 102 that sensor 29 will also be off, and sensor 1 on. This condition will indicate a defect in accordance with the logic given above.

It can be seen that using sensors 1, 17, and 29 for the detection of undersized traces as described above, would be operable only if the board being inspected contained traces having a general direction perpendicular to the line between sensors 17 and 29. In order to accommodate circuit board traces which proceed in other directions, it is preferred that other groups of three sensors having other orientations be provided. A plurality of sensors arranged in two concentric circles such as sensors 1 through 30 illustrated in FIG. 1 provides a sufficient number of groups having differing orientations as to result in a substantially omnidirectional detection system. In boolean algebra notation, an undersize trace, denoted by the letter C, may be indicated as follows:

$$C = (1 \cdot \overline{29} \cdot \overline{17}) + (2 \cdot \overline{30} \cdot \overline{18}) + (3 \cdot \overline{16} \cdot \overline{19}) +$$
$$(4 \cdot \overline{17} \cdot \overline{20}) + (5 \cdot \overline{18} \cdot \overline{21}) + (6 \cdot \overline{19} \cdot \overline{22}) +$$
$$(7 \cdot \overline{20} \cdot \overline{23}) + (8 \cdot \overline{21} \cdot \overline{24}) + (9 \cdot \overline{22} \cdot \overline{25}) +$$
$$(10 \cdot \overline{23} \cdot \overline{26}) + (11 \cdot \overline{24} \cdot \overline{27}) + (12 \cdot \overline{25} \cdot \overline{28}) +$$
$$(13 \cdot \overline{26} \cdot \overline{29}) + (14 \cdot \overline{27} \cdot \overline{30}) + (15 \cdot \overline{28} \cdot \overline{16})$$

Equation 1

It can be seen that each outer circle sensor has two associated middle circle sensors forming a group of three sensors having the same geometric relationship as sensors 1, 17, and 29, except in varying orientations. An undersized trace having any direction will be detected by one or more of these groups in the course of a complete scan of the area. If, at any time during the scan, one of the outer circle sensors is on while both of its associated middle circle sensors are off, a possible defect will be signalled.

With normal sized traces and voids such as are commonly encountered, the logic as noted in Equation 1 works very well. However, in the case of traces approaching the minimum line width which contain small voids near the center of the trace, there is a possibility that the defect will be missed (assuming that the A enable logic to be discussed later is being used). This possibility can be avoided by additional logical analysis. Instead of only one group of two middle circle sensors being associated with each outer circle sensor, two or three groups of two may be so associated. For example, in addition to sensors 17 and 29, the groups of sensors 16 and 28, and 18 and 30 may be associated with sensor 1, an acceptable trace requiring that at least one sensor from each of the three groups of two be on whenever sensor 1 is on. The complete logic is then represented by the boolean equation:

$$C = 1 \cdot [(\overline{28} \cdot \overline{16}) + (\overline{29} \cdot \overline{17}) + (\overline{30} \cdot \overline{18})] +$$
$$2 \cdot [(\overline{29} \cdot \overline{17}) + (\overline{30} \cdot \overline{18}) + (\overline{16} \cdot \overline{19})] +$$
$$3 \cdot [(\overline{30} \cdot \overline{18}) + (\overline{16} \cdot \overline{19}) + (\overline{17} \cdot \overline{20})] +$$
$$4 \cdot [(\overline{16} \cdot \overline{19}) + (\overline{17} \cdot \overline{20}) + (\overline{18} \cdot \overline{21})] + \ldots +$$
$$15 \cdot [(\overline{27} \cdot \overline{30}) + (\overline{28} \cdot \overline{16}) + (\overline{29} \cdot \overline{17})]$$

Equation 2

As so far explained, it will be apparent to those skilled in the art that there is a serious problem associated with the logic described. As the acceptable trace 100 is scanned by the sensor array, at some point in time a sensor on the outer circle of sensors, for example sensor 4, will be on, and all associated middle circle sensors (numbers 16 through 22) will be off. Thus a defect will be signalled even though no defect, in fact, exists. This difficulty can be avoided by disabling the defect logic when the sensor array is substantially off center of a trace. Or, stating the proposition in reverse, enabling the logic only when the detector array is substantially centered on a trace. An inner circle of sensors, sensors 31 through 36 may be provided for this purpose. The diameter of the inner circle of sensors 31 through 36 should be somewhat less than the minimum trace width and all logically added together to provide an enable signal to the defect logic only when all are on. If the radius of the outer circle of sensors is then made such that the difference in radii between the outer and inner circles of sensors is equal to the minimum trace spacing, the above described problem will be avoided, and in addition, the logic will signal a defect if the trace spacing falls below the minimum allowed.

The number of sensors in the inner circle is arbitrary, one only located at the center of the array being sufficient to avoid the logical problem discussed above. However, by providing a plurality of inner circle sensors which define a reasonably smooth circle, it becomes practical to utilize the inner and outer circle sensors to detect undersize trace spacing, as described above.

The enable logic, in boolean notation is:

$$A = 31 \cdot 32 \cdot 33 \cdot 34 \cdot 35 \cdot 36$$

Another common defect found on circuit boards is a broken trace such as break 107 in FIG. 2. As can be seen in FIG. 2, there will be a time when only three outer circle sensors, all adjacent, are on, that is, twelve outer circle sensors in sequence will be off, at the same time the enable signal from sensors 31 through 36 is being provided. This situation will exist in the case of a broken trace, but if the trace ends in an enlarged pad, there will never be a time when so many outer circle sensors in sequence are off at the same time all of the inner circle sensors are on.

The logic for detecting a line break (B) in boolean notation can be stated as follows:

$$B = \bar{1} \cdot \bar{2} \cdot \bar{3} \cdot \bar{4} \cdot \bar{5} \cdot \bar{6} \cdot \bar{7} \cdot \bar{8} \cdot \bar{9} \cdot \overline{10} \cdot \overline{11} +$$
$$\bar{2} \cdot \bar{3} \cdot \bar{4} \cdot \bar{5} \cdot \bar{6} \cdot \bar{7} \cdot \bar{8} \cdot \bar{9} \cdot \overline{10} \cdot \overline{11} \cdot \overline{12} +$$
$$\bar{3} \cdot \bar{4} \cdot \bar{5} \cdot \bar{6} \cdot \bar{7} \cdot \bar{8} \cdot \bar{9} \cdot \overline{10} \cdot \overline{11} \cdot \overline{12} \cdot \overline{13} +$$
$$\bar{4} \cdot \bar{5} \cdot \bar{6} \cdot \bar{7} \cdot \bar{8} \cdot \bar{9} \cdot \overline{10} \cdot \overline{11} \cdot \overline{12} \cdot \overline{13} \cdot \overline{14} + \ldots +$$
$$\overline{15} \cdot \bar{1} \cdot \bar{2} \cdot \bar{3} \cdot \bar{4} \cdot \bar{5} \cdot \bar{6} \cdot \bar{7} \cdot \bar{8} \cdot \bar{9} \cdot \overline{10}$$

Equation 3

Figure 3:
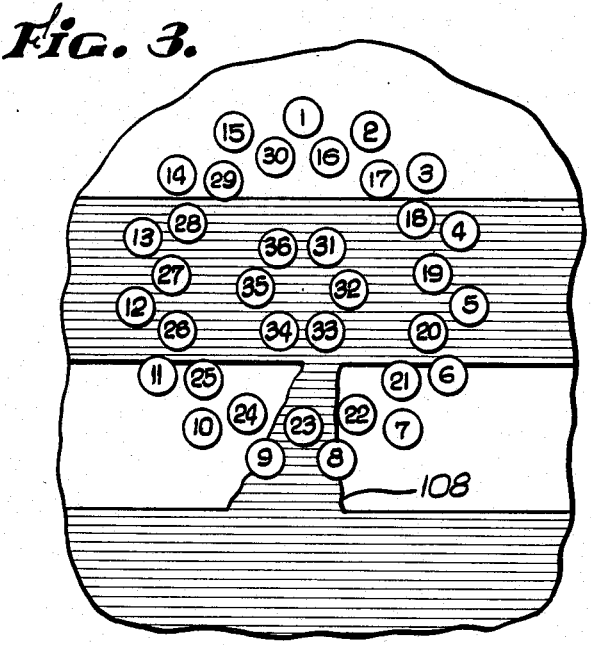
FIG. 3 is a face view of the sensor assembly of a first embodiment of the invention with a defective trace superimposed thereon.
Figure 4:
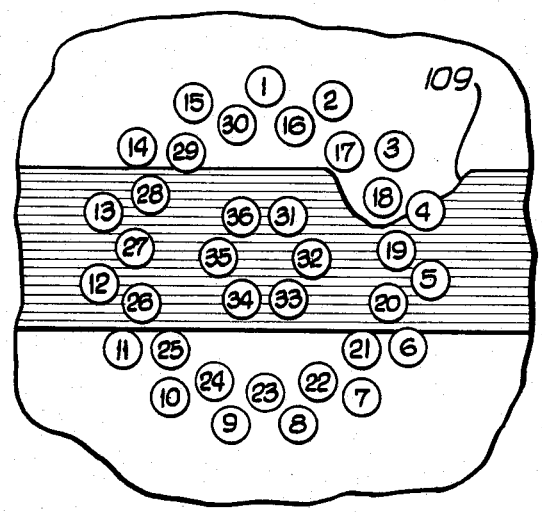
FIG. 4 is a face view of the sensor assembly of a first embodiment of the invention with a defective trace superimposed thereon.

FIGS. 3 and 4 show examples of two other typical defects which often appear on circuit boards. FIG. 3 shows a thin tendril 108 of spurious copper shorting two circuit lines. At the point in the scan cycle shown, sensors 31 through 36 are on, providing the enable signal, and sensor 9 in the outer circle of sensors is also on. Neither of the two middle circle sensors associated with sensor 9 (sensors 22 and 25) are on, however, and a defect is thus indicated.

FIG. 4 shows a nick, or "mousebite", 109 in a trace. Here, although sensor 5 in the outer circle is on, neither sensor 18 nor 21 in the middle circle is on, indicating a defect.

What has been described to this point is an array of sensors or sensed points to which logical analysis can be applied to determine whether or not, at a particular region of a circuit board certain conditions exist which are inconsistent with an acceptable circuit board. These conditions exist if the enable signal (A) is on and either a certain number of outer circle sensors in sequence are on (B), or an outer circle sensor but neither of the sensors in one or more of its groups of associated middle circle sensors are on (C). In boolean notation this is stated:

$$D(\text{Defect}) = A \cdot (B + C)$$

It should be noted that while the invention has been described in connection with an array of sensors having 15 sensors in each of the outer and middle circles, and 6 in the inner circle, the number of sensors in each circle is arbitrary, and logical sequences in accordance with the principles disclosed herein can be devised using other numbers of sensors, either odd or even. However, an odd number of sensors in the outer circle offers some advantage over an even number. For example, an odd number of sensors in the outer and middle circles provides more orientations for the three sensor groups, since with an even number of sensors on the circles, diametrically opposed groups have the same orientation, but with an odd number, no such duplication exists.

As previously noted, various logic plans may be used to detect trace defects which commonly appear. For example, if an even number of sensors is used in the outer circle of sensors, a break in the trace may be detected by a logic sequence which signals a possible break in the trace unless at least two alternate (e.g., odd numbered) sensors in the outer circle are on. In boolean notation, for an 18 sensor outer circle, the equation would be as follows (the outer circle sensors being numbered consecutively 1-18):

$$B = [(\bar{1} + \bar{3})(\bar{5})(\bar{7})(\bar{9})(\overline{11})(\overline{13})(\overline{15})(\overline{17})] +$$
$$[(\bar{5} + \bar{7})(\bar{1})(\bar{3})(\bar{9})(\overline{11})(\overline{13})(\overline{15})(\overline{17})] +$$
$$[(\bar{9} + \overline{11})(\bar{1})(\bar{3})(\bar{5})(\bar{7})(\overline{13})(\overline{15})(\overline{17})] +$$
$$[(\overline{13} + \overline{15})(\bar{1})(\bar{3})(\bar{5})(\bar{7})(\bar{9})(\overline{11})(\overline{17})] +$$
$$[(\bar{1})(\bar{3})(\bar{5})(\bar{7})(\bar{9})(\overline{11})(\overline{13})(\overline{15})(17)]$$

The same array of sensors as previously described for use in detecting defects in traces can be used to detect defects in pads. By changing the effective size of the array so that the diameter of the middle ring of sensors is equal to the minimum pad diameter, defects in pads may be detected. Under these circumstances, a circuit trace width will be slightly less than the distance between two outer circle sensors, and therefore no line emanating from a pad will cause more than one outer circle sensor to be one. Also, no individual line or line junction can turn on all of the sensors 31 through 36 to provide an enable signal.

The logic equations which indicate a pad defect (D) are therefore:

$$A \text{ (Enable)} = 31 \cdot 32 \cdot 33 \cdot 34 \cdot 35 \cdot 36 \quad \text{Equation 4}$$

$$E \text{ (}\overline{\text{Enable}}\text{)} = (1 \cdot 2) + (2 \cdot 3) + (3 \cdot 4) + \ldots$$
$$+ (14 \cdot 15) + (15 \cdot 1) \quad \text{Equation 5}$$

$$P \text{ (Test)} = 17 \cdot 18 \cdot 19 \cdot 20 \cdot 21 \cdot 22 \cdot 23 \cdot 24 \cdot 25 \cdot 26 \cdot 27 \cdot 28 \cdot 29 \cdot 30 \quad \text{Equation 6}$$

$$D \text{ (Defect)} = A \cdot \bar{E} \cdot \bar{P} \quad \text{Equation 7}$$

The A enable signal indicates that the array of sensors is sensing trace material of substantial size (i.e., larger than a line), the $\bar{E}$ enable signal indicates that the material being sensed is contained within the outer circle of sensors (no two adjacent outer circle sensors are on), and the $\bar{P}$ signal indicates that the size is smaller than the minimum pad size, or that the pad has some other defect such as a "mousebite" (one or more middle circle sensors off). A combination of A, $\bar{E}$ and $\bar{P}$ thus signals that the array is covering a pad, but that a defect exists.

Figure 5:
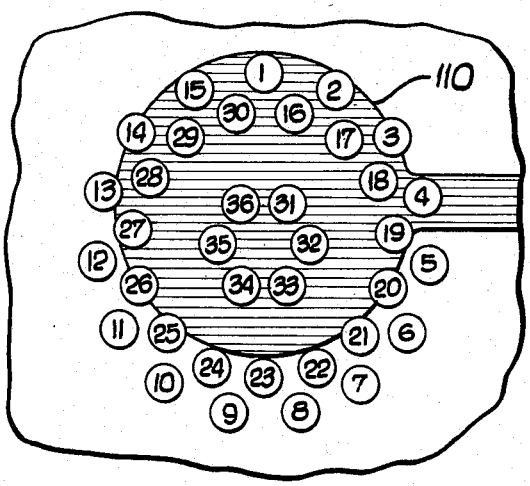
FIG. 5 is a face view of the sensor assembly of a first embodiment of the invention with the image of a circuit board pad superimposed thereon.
Figure 6:
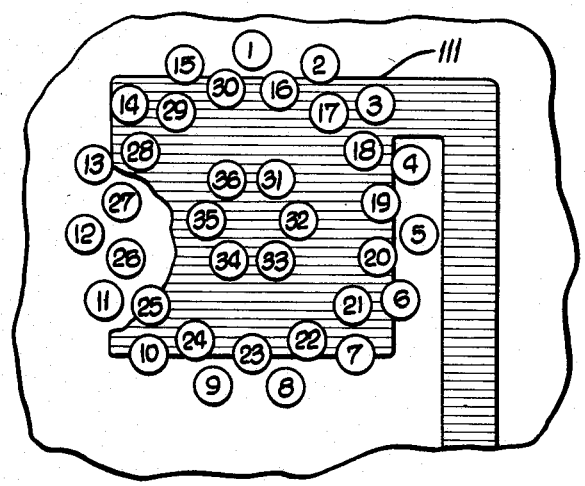
FIG. 6 is a face view of the sensor assembly of a first embodiment of the invention with a defective square circuit board pad superimposed thereon.

FIG. 5 shows how an acceptable pad 110, not centered over the sensing array, will cause an E signal preventing a defect from being signalled. In this case sensors 14, 15, 1, 2 3, and 4 are all on. FIG. 6 shows an acceptably sized pad with a "mousebite", causing middle circle sensors 26 and 27 to be off and a $\bar{P}$ signal to appear. It may be noted that the corners of the square pad 111 in FIG. 6 energize only a single outer circle sensor each so that the $\bar{E}$ enable signal is generated even though the pad being inspected is square.

The above description of the sensing patterns and logical sequences involved in the detection of defects in accordance with the present invention has been presented for purposes of ease of explanation and understanding as if an appropriate assembly of sensors was physically moved over the area being inspected. Such an arrangement, while useful for explanatory purposes, may not be convenient for many, if not most, applications of the invention.

A presently preferred scanning means is described below which invloves projecting a light image of the area being inspected on a stationary group of sensors, the image being caused to move over the sensor assembly in accordance with a scanning plan. In this connection it may be noted that while a convenient scanning routine is a raster as is used in forming a television image, no particular plan is required to accomplish the desired inspection, so long as the entire area being inspected is covered during the inspection cycle.

The presently preferred scanning means is described in connection with the inspection of a printed circuit board. Light reflecting off the shiny surface of conductor material in contrast with a dull board background provides sufficient light differential for operating commercially available sensors. Photographic negatives of printed circuit board patterns can be conveniently inspected by placing the negative on a reflecting surface, such as silvered mylar and reversing the sensing logic i.e. high light level indicating lack of conductor instead of vice versa).

Figure 7:
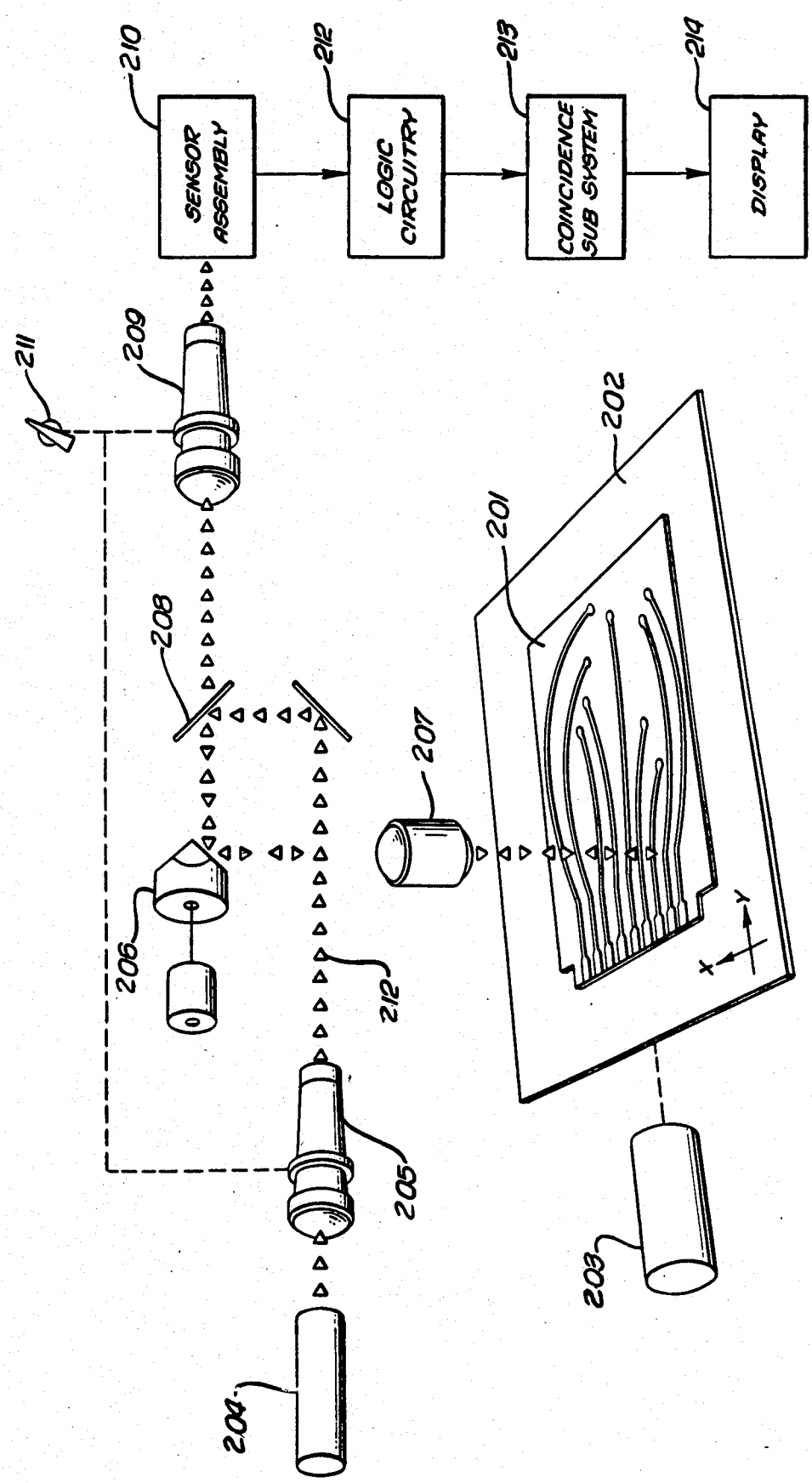
FIG. 7 is a combination mechanical schematic diagram and electrical block diagram of the present invention.

Refer now to FIG. 7 which illustrates the presently preferred scanning means. A printed circuit board 201 under inspection is placed on a movable horizontal table 202. Motor 203 drives the table 202 in the "Y" direction as shown, through conventional gearing (not shown). This movement provides the equivalent of the "vertical" scan of a television picture. The scan in the "X" direction (comparable to a "horizontal" television scan) is a spot of light which originates at laser 204. The light beam path is indicated by triangles 212. Zoom lens 205 is adjusted to cause a spot of light slightly greater than three minimum conductor widths to fall on the circuit board under inspection. The spot size is proportional to the ratio of the focal lengths of zoom lens 205 and field lens 207.

The laser beam may be reflected off such mirrors as is convenient to direct the light in the desired directions as shown, including a beam splitting mirror 208. Mirror 208 may be a half silvered mirror, as is conventional, but preferably is clear with a small mirrored area in the center. Light from laser 204 is focused to a small spot at mirror 208 so that the entire spot reflects off the small mirrored area and onto tetrahedron 206. The scanning motion is provided by the rotating mirrored tetrahedron 206 which directs the laser beam through field lens 207 and onto the surface to be inspected. Field lens 207 converts the angular deviation of the input beam generated by the tetrahedron 206 into a linear displacement at the printed circuit board. The speed of rotation of motor 203 is correlated with the speed of the tetrahedron 206 so that the line density of the scanning raster is sufficient to detect the defects desired. Typically, the "Y" motion will be such that table 202 will advance one sensor diameter or less for each "X" scan so that each individual sensor will view the entire circuit board area during the inspection cycle, and no area will be missed. While it is preferable that the "X" and "Y" directions be perpendicular, and that the "X" and "Y" scans be synchronized, such is not required since a satisfactory scanning raster can be achieved even though the directions of motion are not perpendicular and not in synchronism. It is only necessary that the entire surface to be inspected be within the view of each sensor at some time during the inspection cycle.

Light reflected from the surface of circuit board 201 passes back through the field lens 207, reflects off tetrahedron 206, and passes through beam splitter 208 to zoom lens 209. The returning light beam reflected off tetrahedron 206 has a relatively large size so that the small mirrored portion of beam splitter 208 does not interfere with the passage of light to zoom lens 209. Zoom lens 309 focuses an image of circuit board 201 on detector assembly 210. The image size is proportional to the ratio of focal lengths of lenses 207 and 209.

Detector assembly 210 is comprised of a plurality of sensors disposed in a pattern as required for the particular embodiment of the invention involved. In the case of the embodiment described in connection with FIGS. 1 through 6, 36 sensors are utilized in the pattern as shown.

Commonly encountered circuit boards may have trace widths in the range of 0.004 inch to 0.020 inch. Economical optics are available to form an image of the requisite area of such boards about ⅛ inch in diameter, however, the sensors necessary to form an array such as described herein with the diameter of the outer circle of sensors somewhat less than ⅛ inch would be smaller than are normally available. This difficulty has been overcome by using the economical optical components available to form an image of a convenient size on the face of a fiber optics transmission line, and conducting the light therefrom to larger sensors via fiber optics.

The focal length of zoom lens 209 may be conveniently coordinated with the focal length of zoom lens 205 so that a single adjustment knob 211 adjusts both the diameter of the spot of light falling on board 201 and the size of the image focused on sensor assembly 210. The spot size will then always be of sufficient size to provide illumination of all sensors in the sensing pattern irrespective of the size of the traces being inspected. Coupling zoom lenses 205 and 209 also insures that the same amount of light falls on a sensor regardless of the image magnification.

Figure 8:
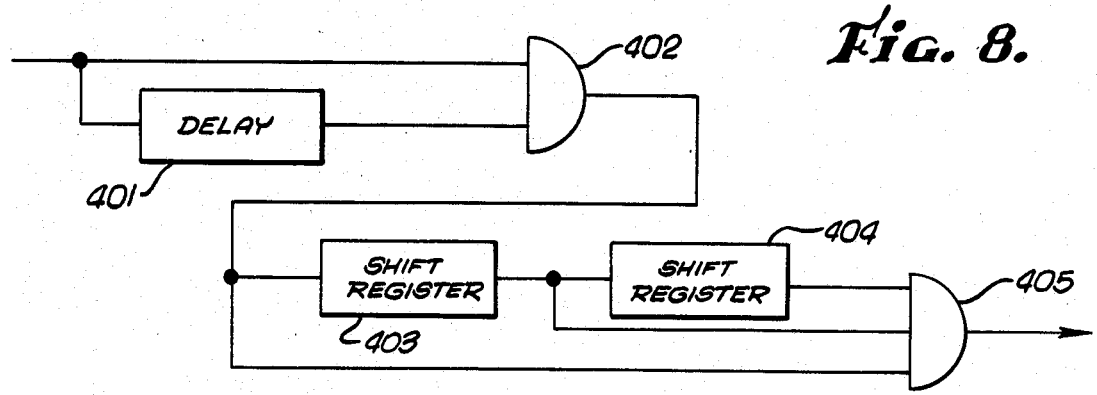
FIG. 8 is an electrical block diagram of the coincidence subsystem.

There are many infinitesimal defects in the average printed circuit board which are unimportant and should be ignored, but which could trigger a defect response if one just happened to be scanned across the array in exactly the right position. In addition, noise, both electrical and optical, can occasionally trigger a defect response. The coincidence subsystem shown in FIG. 8 avoids this problem by assuring that a defect signal is generated only by a defect having certain preestablished minimum dimensions. In the direction along the line scan, the raw D or defect signal is delayed in delay 401, the output of which is combined with the raw D signal in AND gate 402. Gate 402 produces an output only if the D signal lasts for the delay time of delay 401 or, in other words, is longer than the scan line length corresponding to delay 401. By adjusting the delay time, the minimum defect size (in the x direction) can be set.

The output of AND gate 402 is fed through two 8 stage shift registers 403 and 404. The shift registers 403 and 404 are controlled by a clock signal which has a repetition rate eight times the line scan rate of the scanning system. Thus, a defect signal will pass out of shift register 403 exactly one line after it was applied at the input of shift register 403. Similarly, shift register 404 delays the defect signal the time of one line scan. AND gate 405 which accepts the outputs from AND gate 402, shift register 403, and shift register 404, will produce an output only if a defect signal D lasts for more than the delay time of delay 401 on three successive scans. By adding more shift registers, the minimum detectable defect size can be made, 4, 5 or more lines long in the y direction.

The first preferred embodiment of the scanning portion of the present invention described above involves scanning the region to be inspected with an array of sensors which simulataneously view the points used to establish whether or not each particular area on the board meets the criteria for acceptance. A second embodiment of the scanning portion of the invention involves scanning the points on the board to be inspected serially in raster fashion, the data from each point viewed being stored in memory means. Logical analysis, as previously described, is performed on the stored data to establish conformance or nonconformance with the preestablished criteria.

A "flying spot" scanning system could be used to scan the area being inspectedin the manner described, however, for purposes of example and second embodiment of the invention will be explained using a solid state line scanner. A solid state line scanner is comprised of a row of photodiodes, each with an associated storage capacitor on which the photocurrent is integrated. The integrated photocurrent on each capacitor is multiplexed onto an an output line by use of a shift register. Solid state line scanners are well kown in the art and will not be explained here in detail. By moving the line scanner along the board in a direction perpendicular to the row of photodiodes, each point on the board, one by one, can be scanned in sequence.

Figure 9:
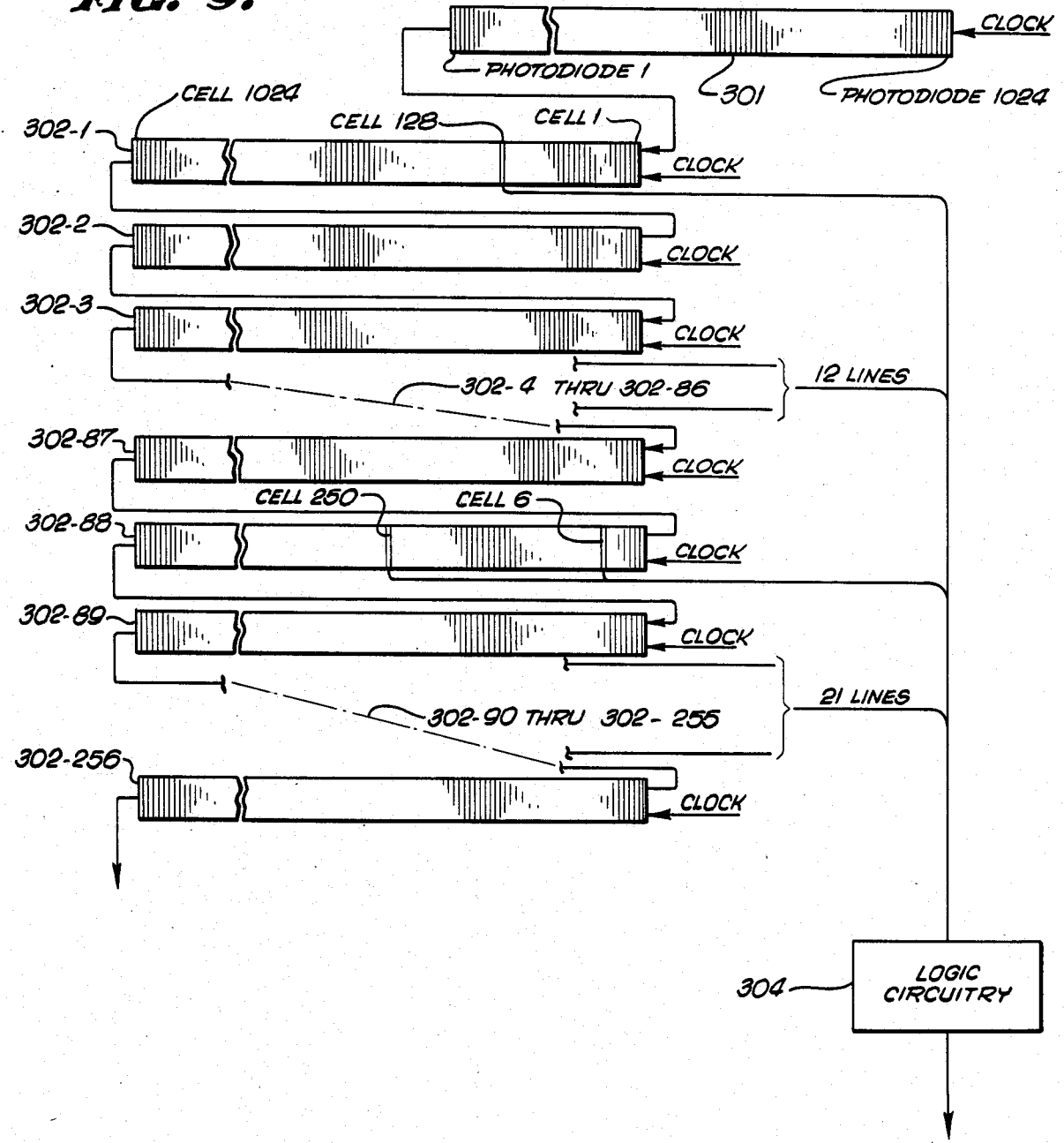
FIG. 9 is an electrical block diagram of a second embodiment of the scanning portion of the invention.

Referring to FIG. 9, which schematically shows a line scanner 301 having 1024 photodiodes, each diode being 0.001 inch wide. The line scanner will therefore scan a section of the board being inspected 1.024 inches wide. Clock means (not shown) shifts data out of line scanner 301 at a continuous rate such that one line of data (1024 points) is shifted out as the line scanner moves 0.001 inches (perpendicular to the row of photodiodes). A complete scan of the board will therefore result in data representing the presence or absence of trace material on the board at points 0.001 apart. The line scanner data is coupled to a group of shift registers 302-1 through 302-256. Each shift register in the group has 1024 cells, and the output of each shift register feeds into the input of the next, as shown in FIG. 9. The cells of shift registers 302-1 through 302-256 can be thought of as forming a matrix of cells 1024 cells wide by 256 cells high. At any instant, the cells of shift registers 302-1 through 302-256 contain data from an area on the board 0.256 inches long by 1.024 inches wide. Assuming that the system has been in operation for enough time to fill the shift registers, and that during a particular scan, have data from photodiodes 1 through 256 of line scanner 301 have been shifted into shift register 302-1, it can be seen that the matrix comprised of cells 1 through 256 of shift registers 302-1 through 302-256 (subsequently referred to as matrix 303) contains information as to the existence of conductor or substrate at each point in the 0.256 inch by 0.256 inch area behind photodiodes 1 to 256 of the line scanner. At the end of the line scan, i.e., when data from photodiode 1024 has been shifted from the line scanner into shift register 302-1, the matrix 303 contains data from the 0.256 inch by 0.256 inch area behind photodiodes 768 through 1024. On the next line scan the matrix 303 will again contain a map of a 0.256 inch square area which moves across the board as before, except that it is one scan line distance advanced (0.001 inch).

As indicated schematically in FIG. 9, certain of the cells in shift registers 302-1 through 302-256 are coupled to the logic circuitry 304. These cells are selected so that at any instant the cells so coupled contain data from points on the board under test which have the same geometric relationships as sensors 1 through 36 described in connection with FIGS. 1 through 4.

For example, the position of sensor 1 corresponds to shift register 302-1, cell 128; the position of sensor 4 corresponds to shift register 302-88, cell 6; the position of sensor 8 corresponds to shift register 302-253, cell 10; and position of sensor 13 corresponds to shift register 302-88, cell 250. The positions corresponding to sensors 1, 4 and 13 are illustrated in FIG. 9. Since the shift register cells contain data on 0.001 inch centers, it follows that each of the 36 sensor positions can be duplicated in matrix 303 within 0.0005 inches of its theoretical position.

The state of the selected cells corresponding to the 36 positions making up the circular sensing pattern is coupled to logic circuitry 304 where the relative states of the cells are analyzed to determine whether a defect exists.

By applying the same logic equations as previously discussed to the data appearing at logic circuitry 304, defects in the circuit boards can be detected in the same way as described above. A complete pattern for analysis is available on each line scan only after data from the first 256 photodiode has beem shifted into shift register 302-1, which means that the effective scan is 0.768 inches wide.

As noted above, the line scanner is moved 0.001 inch per line scan, in a direction perpendicular to the line being scanned. Each time the scanner reaches the end of the area being inspected, it is indexed 0.768 inches sideways and the adjacent 0.768 inch wide strip of board scanned. In this way an entire area to be inspected can be covered.

While the scanning means just disclosed has been described in connection with an effective diameter for the outer circle of sensors of 0.256 inches, by the use of optics and also changing the speed of the line scanner relative to the board under test, the effective diameter of the sensing circles can be adjusted to whatever is necessary to inspect any particular board.

I claim:
1. A line defect detection system which comprises:
   means for sensing the presence or absence of a line at a plurality of points in an area to be inspected, said points being in a circular pattern, said plurality of points including:
   (i) first and second points spaced apart a distance related to the minimum acceptable line width; and
   (ii) a third point between said first and second points;
   means responsive to the relative states of said sensing means for recognizing the presence of a line segment having a width less than said acceptable line width; and
   means for determining whether the center of said circular pattern is on a line.
2. The line defect detection system as recited in claim 1 wherein said means for determining whether the center of said circular pattern is on a line comprises means for sensing the presence or absence of a line at one or more points inside said circular pattern.
3. The line defect detection system as recited in claim 1 where all of said points are sensed simultaneously, and further including means for causing the center of said circular pattern to scan a region being inspected.

4. The line defect detection system as recited in claim 3 where the means for causing the center of said circular pattern to scan moves said center in raster fashion.

5. The line defect detection system as recited in claim 1 where said sensing means comprises means for scanning a region to be inspected in raster fashion and further including:
means for storing data from said sensing means; and
means for retrieving data from said storing means, said retrieved data being data representing the presence or absence of a line at said pluralities of points.

6. The line defect detection system as recited in claim 5 where said means for retrieving data retrieves all of the data representing circular pattern which have one center simultaneously.

7. The line defect detection system as recited in claim 5 where said storing means is a group of shift registers and where said means for retrieving data is responsive to the states of a plurality of stages of said shift registers.

8. The line defect detection system as recited in claim 1 and further including means for inhibiting the signalling of a defect smaller than a predetermined size.

9. A line defect detection system which comprises:
a plurality of sensors, each for sensing the presence or absence of said line in an area, said sensors sensing areas in a preestablished pattern, said plurality of sensors including:
(i) first and second sensors spaced apart a distance related to the minimum acceptable line width; and
(ii) a third sensor between said first and second sensors;
means responsive to the relative states of said sensors for recognizing the presence of a line segment having a width less than said minimum line width; and
scanning means for causing the region containing said line to be traversed by said pattern, said plurality of sensors including a plurality of sensors arranged to sense a pattern of areas comprised of two concentric circles, said first and second sensors sensing areas on the smaller of said two concentric circles and said third sensor sensing an area on the larger of said two concentric circles.

10. A line defect detection system which comprises:
a plurality of sensors arranged in a circular pattern, each for sensing the presence or absence of said line in an area, said sensors sensing areas in a preestablished pattern, said plurality of sensors including:
(i) first and second sensors spaced apart a distance related to the minimum acceptable line width; and
(ii) a third sensor between said first and second sensors;
means responsive to the relative states of said sensors for recognizing the presence of a line segment having a width less than said minimum line width;
scanning means for causing the region containing said line to be traversed by said pattern; and
means for detecting whether said circular pattern is substantially centered on a line.

11. A line defect detection system which comprises:
a plurality of sensors, each for sensing the presence or absence of said line in an area, said sensors sensing areas in a preestablished pattern, said plurality of sensors including:
(i) first and second sensors spaced apart a distance related to the minimum acceptable line width; and
(ii) a third sensor between said first and second sensors;
means responsive to the relative states of said sensors for recognizing the presence of a line segment having a width less than said minimum line width, the relative states of said sensors corresponding to a line segment having a width less than said minimum acceptable line width comprising said first and second sensors sensing an absence of said line and said third sensor sensing presence of said line; and
scanning means for causing the region containing said line to be traversed by said pattern.

12. The line defect detection system as recited in claim 11 and further including means for inhibiting the signalling of a defect smaller than a predetermined size.

13. The line detection system as recited in claim 11 where said third sensor is equally spaced from said first and second sensors.

14. The line defect detection system as recited in claim 11 where said plurality of sensors includes a plurality of sensors arranged to sense a pattern of areas comprised of two concentric circles, said first and second sensors sensing areas on the smaller of said two concentric circles and said third sensor sensing an area on the larger of said two concentric circles.

15. The line defect detection system as recited in claim 14 wherein each of said two concentric circles includes sensors 1 through n, n being an even number, and further including means responsive to the relative states of said sensors for detecting the absence of line sensing by at least two odd numbered sensors on the outer of said concentric circles.

16. The line defect detection system as recited in claim 15 and further including at least one additional sensor disposed to sense the presence or absence of said line inside said concentric circular pattern, said additional sensors inhibiting the operation of detecting a defect unless said additional sensors detect the presence of a line.

17. The line defect detection system as recited in claim 11 where said plurality of sensors includes a plurality of sensors arranged in a circular pattern.

18. The line defect detection system as recited in claim 17 and further including means for detecting whether said circular pattern is substantially centered on a line.

19. The line defect detection system as recited in claim 18 wherein said means for detecting whether said circular pattern is substantially centered on a line comprises at least one sensor disposed to sense areas in the central region of said circular pattern.

20. The line defect detection system as recited in claim 17 and further including means responsive to the relative states of said sensors for detecting the absence of line sensing by a predetermined number of contiguous sensors on said circular pattern.

21. The line defect detection system as recited in claim 11 where said sensors are responsive to light.

22. The line defect detection system as recited in claim 21 where said scanning means comprises:
a source of light;
means for impinging a spot of light from said source on the medium containing the line being inspected;

a moving mirror interposed between said source of light and said medium whereby said spot of light is made to move across said medium; and means for focusing an image of said spot of light on said sensors.

23. The line defect detection system as recited in claim 22 wherein said moving mirror causes said spot of light to move across said medium repeatedly, and further including means for causing said spot of light to move across changing areas of said medium.

24. The line defect detection system as recited in claim 23 where said means for causing said spot of light to move across changing areas of said medium comprises means for moving said medium in a direction other than the direction of motion of said spot of light whereby a scanning raster is formed.

25. The line defect detection system as recited in claim 24 and further including adjusting means for adjusting the size of said image.

26. The line defect detection system as recited in claim 25 where light from said spot is reflected off said moving mirror.

27. The line defect detection system as recited in claim 26 where said moving mirror is a rotating polyhedron.

28. The line defect detection system as recited in claim 27 and further including adjusting means for adjusting the size of said spot.

29. The line defect detection system as recited in claim 28 where said adjusting means for adjusting the size of said spot and the adjusting means for adjusting the size of said image are coupled.

30. The line defect detection system as recited in claim 29 wherein said image is formed at a plane, and further including a fiber optics link conducting light from said image to said sensors said sensors being located away from said plane.

31. The line defect detection system as recited in claim 22 where said plurality of sensors includes a plurality of sensors arranged to sense a pattern of areas comprised of two concentric circles, first and second sensors sensing areas on the smaller of said two concentric circles and said third sensor sensing an area on the larger of said two concentric circles.

32. The line defect detection system as recited in claim 31 wherein each of said two concentric circles includes sensors 1 through n, n being an even number, and wherein a logical condition comprising the absence of line sensing by at least two odd numbered sensors on the outer of said concentric circles corresponds to a defect.

33. The line defect detection system as recited in claim 32 and further including at least one additional sensor disposed to sense the presence or absence of said line inside said concentric circular pattern, said sensor inhibiting the operation of detecting a defect unless said additional sensors detect the presence of a line.

34. A line defect detection system for detecting breaks in lines which comprises:
means for sensing the presence or absence of a line at a plurality of points in an area to be inspected, said plurality of points being arranged in a circle; and
means responsive to said sensing means for determining whether the number of contiguous points at which an absence of a line is sensed is greater than a predetermined number.

35. The line defect detection system as recited in claim 34 and further including means for determining whether the center of said circle is on a line.

36. The line defect detection system as recited in claim 34 where said means for determining whether the center of said circle is on a line comprises means for sensing the presence or absence of a line at one or more points within said circular pattern.

37. A line defect detection system which comprises:
means for sensing the presence or absence of a line at a plurality of points in an area to be inspected, said points being in a circular pattern, said plurality of points including:
(i) first and second points spaced apart a distance related to the minimum acceptable line width; and
(ii) a third point between said first and second points; and
means responsive to the relative states of said sensing means for recognizing the presence of a line segment having a width less than said minimum acceptable line width, the relative states of said sensing means corresponding to a line segment having a width less than said minimum acceptable line width comprising sensing an absence of said line at said first and second points and a presence of said line at said third point.

38. The line defect detection system as recited in claim 37 and further including means for determining whether the center of said circular pattern is on a line.

39. The line defect detection system as recited in claim 37 where said plurality of points includes a plurality of points arranged in two concentric circles, said first and second points being on one of said two concentric circles and said third point being on the other of said two concentric circles.

40. The line defect detection system as recited in claim 39 where said first and second points are on the smaller of said two concentric circles.

41. A printed circuit board trace defect detection system which comprises:
a first plurality of sensors each for sensing the presence or absence of a trace in an area of a printed circuit board, the sensed areas being symmetrically disposed on a first circle;
a second plurality of sensors, each sensing the presence or absence of a trace on an area on a printed circuit board, said second plurality of sensors being equal in number to said first plurality of sensors and each being disposed to sense an area of said circuit board equally distant from two of said first plurality of sensors and being on a second circle concentric with an inside said first circle, the areas sensed by first and second pluralities of sensors comprising a sensing pattern;
scanning means for causing said sensing pattern to traverse said printed circuit board; and
logic means responsive to the relative states of said sensors to produce a signal whenever said states are inconsistent with at least one preestablished criterion, one of said states inconsistent with a preestablished criterion being the sensing of the presence of a trace by a first sensor disposed on said first circle accompanied by the sensing of absence of a trace by both of two sensors disposed on said second circle, said two sensors and said first sensor being a predetermined group.

42. The printed circuit board trace defect detection system as recited in claim 41 wherein there are sensors numbered 1 to n on said first circle, n being an even number, and one of said states inconsistent with a preestablished criterion is the sensing of the presence of a trace by less than two odd numbered sensors on said first circle.

43. The printed circuit defect detection system as recited in claim 41 wherein a logical condition comprising a predetermined number of contiguous sensors on one of said concentric circles sensing the absence of a trace corresponds to a condition inconsistent with pre-established criteria.

44. The printed circuit board defect detection system as recited in claims 41, 42 or 43 and further including means for detecting whether said sensing pattern is substantially centered on a line.

45. The printed circuit board defect detection system as recited in claim 44 wherein said means for detecting whether said sensing pattern is substantially centered on a line comprises at least one sensor disposed to sense areas in the central region of said circular pattern.

46. The line defect detection system as recited in claims 41, 42 or 43 and further including means for inhibiting the signalling of a defect smaller than a predetermined size.

47. The printed circuit board trace defect detection system as recited in claims 41, 42, or 43 where said sensors are responsive to light.

48. The printed circuit board trace defect detection system as recited in claim 47 where said scanning means comprises:
   a source of light;
   means for impinging a spot of light from said source on the printed circuit board being inspected;
   a moving mirror interposed between said source of light and said printed circuit board whereby said spot of light is made to move across said printed circuit board;
   means for focusing an image of said spot of light on said sensors.

49. The printed circuit board trace defect detection system as recited in claim 48 wherein said moving mirror causes said spot of light to move across said printed circuit board repeatedly, and further including means for causing said spot of light to move across changing areas of said circuit board.

50. The printed circuit board trace defect detection system as recited in claim 49 where said means for causing said spot of light to move across changing areas of said circuit board comprises means for moving said circuit board in a direction other than the direction of motion of said spot of light whereby a scanning raster is formed.

51. The printed circuit board trace defect detection system as recited in claim 50 and further including means for adjusting the size of said image.

52. The printed circuit board trace defect detection system as recited in claim 51 where the light forming said image is reflected off said mirror both on the way to said printed circuit board and after being reflected off said printed circuit board.

53. The printed circuit board trace defect detection system as recited in claim 52 where said moving mirror is a rotating polyhedron.

54. The printed circuit board trace defect detection system as recited in claim 53 where said second mirror is interposed between said source of light and said moving mirror, the light from said source of light being focused into a small spot on said second mirror, the size of said second mirror being larger than the size of the returning beam reflected off said moving mirror whereby said second mirror does not completely obstruct said returning beam.

55. A printed circuit board trace defect detection system which comprises:
   sensors 1 through 15 symmetrically disposed to sense a first circular pattern of areas of a printed circuit board;
   sensors 16 through 30 symmetrically disposed to sense a second circular pattern of areas on said printed circuit board, said second circular pattern being concentric with and smaller than said first circular pattern and angularly displaced therefrom approximately 12 degrees, all of said sensors 1 through 30 forming a sensing pattern;
   means for causing said sensing pattern to scan the area of said printed circuit board to be inspected; and
   logic means responsive to the relative states of said sensors for indicating a trace defect, where one of said relative states indicating a trace defect may be stated in boolean notation as follows:

$$\text{indication of trace defect} = 1 \cdot [(\overline{28} \cdot \overline{16}) + (\overline{29} \cdot \overline{17}) + (\overline{30} \cdot \overline{18})] + 2 \cdot [(\overline{29} \cdot \overline{17}) + (\overline{30} \cdot \overline{18}) + (\overline{16} \cdot \overline{19})] +$$
$$3 \cdot [(\overline{30} \cdot \overline{18}) + (\overline{16} \cdot \overline{19}) + (\overline{17} \cdot \overline{20})] +$$
$$4 \cdot [(\overline{16} \cdot \overline{19}) + (\overline{17} \cdot \overline{20}) + (\overline{18} \cdot \overline{21})] + \ldots +$$
$$15 \cdot [(\overline{27} \cdot \overline{30}) + (\overline{28} \cdot \overline{16}) + (\overline{29} \cdot \overline{17})]$$

56. A printed circuit board trace defect detection system which comprises:
   sensors 1 through 15 symmetrically disposed to sense a first circular pattern of areas of a printed circuit board;
   sensors 16 through 30 symmetrically disposed to sense a second circular pattern of areas on said printed circuit board, said second circular pattern being concentric with a smaller than said first circular pattern and angularly displaced therefrom approximately 12 degrees, all of said sensors 1 through 30 forming a sensing pattern;
   means for causing said sensing pattern to scan the area of said printed circuit board to be inspected; and
   logic means responsive to the relative states of said sensors for indicating a trace defect, where one of said relative states indicating a trace defect may be stated in boolean notation as follows:

$$B = \overline{1} \cdot \overline{2} \cdot \overline{3} \cdot \overline{4} \cdot \overline{5} \cdot \overline{6} \cdot \overline{7} \cdot \overline{8} \cdot \overline{9} \cdot \overline{10} \cdot \overline{11} \cdot \overline{12} +$$
$$\overline{2} \cdot \overline{3} \cdot \overline{4} \cdot \overline{5} \cdot \overline{6} \cdot \overline{7} \cdot \overline{8} \cdot \overline{9} \cdot \overline{10} \cdot \overline{11} \cdot \overline{12} \cdot \overline{13} +$$
$$\overline{3} \cdot \overline{4} \cdot \overline{5} \cdot \overline{6} \cdot \overline{7} \cdot \overline{8} \cdot \overline{9} \cdot \overline{10} \cdot \overline{11} \cdot \overline{12} \cdot \overline{13} \cdot \overline{14} +$$
$$\overline{4} \cdot \overline{5} \cdot \overline{6} \cdot \overline{7} \cdot \overline{8} \cdot \overline{9} \cdot \overline{10} \cdot \overline{11} \cdot \overline{12} \cdot \overline{13} \cdot \overline{14} \cdot \overline{15} + \ldots +$$
$$\overline{15} \cdot \cdot \overline{1} \cdot \overline{2} \cdot \overline{3} \cdot \overline{4} \cdot \overline{5} \cdot \overline{6} \cdot \overline{7} \cdot \overline{8} \cdot \overline{9} \cdot \overline{10} \cdot \overline{11}$$

57. The line defect detection system as recited in claims 55 or 56 and further including means for inhibiting the signalling of a defect smaller than a predetermined size.

58. The line defect detection system as recited in claims 55 or 56 and further including means for detecting whether said sensing pattern is substantially centered on a line.

59. The line defect detection system as recited in claim 58 wherein said means for detecting whether said sensing pattern is substantially centered on a line comprises at least one sensor disposed to sense areas in the central region of said circular pattern.

60. A printed circuit board trace defect detection system as recited in claims 55 or 56 and further including adjusting means for adjusting the size of said sensing pattern relative to the area being inspected.

61. A printed circuit board trace defect detection system as recited in claims 55 or 56 wherein said sensors are responsive to light level.

62. A line defect detection system which comprises:
means for sensing the presence or absence of a line at each of a plurality of points in an area to be inspected; and
means responsive to the relative presence or absence of said line at one or more groups of said points for recognizing the presence of a line segment having a width less than the minimum acceptable line width, the points comprising said groups having preestablished geometrical relationships with one another, at least one of said geometrical relationships between points comprising first and second points separated by a distance equal to said minimum acceptable line width, and a third point between said first and second points, the criterion for said recognition comprising an absence of a line at said first and second points and a presence of a line at said third point.

63. A line defect detection system as recited in claims 62 wherein said groups of points form a pattern of points, said pattern including points symmetrically arranged around a central region.

64. A line defect detection system as recited in claim 62 wherein said third point is equidistant from said first and second points.

65. A line defect detection system as recited in claims 62 and further including scanning means whereby said area to be inspected is scanned by said sensing means, points within said area to be inspected being sequentially sensed.

66. A line defect detection system which comprises:
a plurality of sensors, each for sensing the presence or absence of said line in an area, said sensors sensing areas in a preestablished pattern, said plurality of sensors including:
(i) first and second sensors spaced apart a distance related to the minumum acceptable line width; and
(ii) a third sensor between said first and second sensors;
means responsive to the relative states of said sensors for recognizing the presence of a line segment having a width less than said minimum line width;
scanning means for causing the region containing said line to be traversed by said pattern; and
means for inhibiting the signalling of a defect smaller than a predetermined size.

67. Apparatus for inspection of square or circular figures which comprises:
means for sensing the presence or absence of said figure at a plurality of points in the region of said figure, said plurality of points being arranged in two concentric circles, the inner of said circles having a diameter equal to the minimum acceptable smallest dimension of said figure; and
logic means responsive to the relative state of said sensing means for determining if said figure is acceptable, a logic state wherein all of the points on the inner of said concentric circles contain said figure, and no more than a predetermined number of adjacent points on the outer of said circles contain said figure corresponding to an acceptable figure.

68. An apparatus for inspection of square or circular figures as recited in claim 67 and further including means for determining that the center of said concentric circles is on a figure to be inspected.

69. An apparatus for inspection of square or circular figures as recited in claim 68 where said means for determining that the center of said concentric circles is on a figure to be inspected comprises means for sensing the presence or absence of a figure at at least one point within the inner of said concentric circles.

70. A line defect detection system which comprises:
means for sensing the presence or absence of a line at a plurality of points in an area to be inspected, said points being in a circular pattern, said plurality of points including:
(i) first and second points spaced apart a distance related to the minimum acceptable line width; and
(ii) a third point between said first and second points; and
means responsive to the relative states of said sensing means for recognizing the presence of a line segment having a width less than said acceptable line width, said plurality of points including a plurality of points arranged in two concentric circles, said first and second points being on one of said two concentric circles and said third point being on the other of said two concentric circles.

* * * * *